US00PP21406P2

(12) United States Plant Patent
O'Connell

(10) Patent No.: US PP21,406 P2
(45) Date of Patent: Oct. 19, 2010

(54) ***ECHEVERIA* PLANT NAMED 'NEON BREAKERS'**

(50) Latin Name: *Echeveria hybrid*
Varietal Denomination: Neon Breakers

(76) Inventor: Renee O'Connell, 1801 Tierra Libertia, Escondido, CA (US) 92026

( * ) Notice: Subject to any disclaimer, the term of this patent is extended or adjusted under 35 U.S.C. 154(b) by 0 days.

(21) Appl. No.: 12/455,721

(22) Filed: Jun. 6, 2009

(51) Int. Cl.
*A01H 5/00* (2006.01)

(52) U.S. Cl. ..... Plt./373
(58) Field of Classification Search ..... Plt./373
See application file for complete search history.

*Primary Examiner*—Annette H Para

(57) ABSTRACT

A new and distinct *Echeveria* cultivar named 'Neon Breakers' is disclosed, characterized by intensely colorful leaf margins, increased resistance to normal disease and pests encountered in *Echeverias*. The new variety exhibits a robust growth habit due to the increased resistance, and unique continuous growth, not shutting down seasonally, as is typical of *Echveria*. The new variety is an *Echeveria*, typically produced as a garden or container plant.

1 Drawing Sheet

Figure 1:
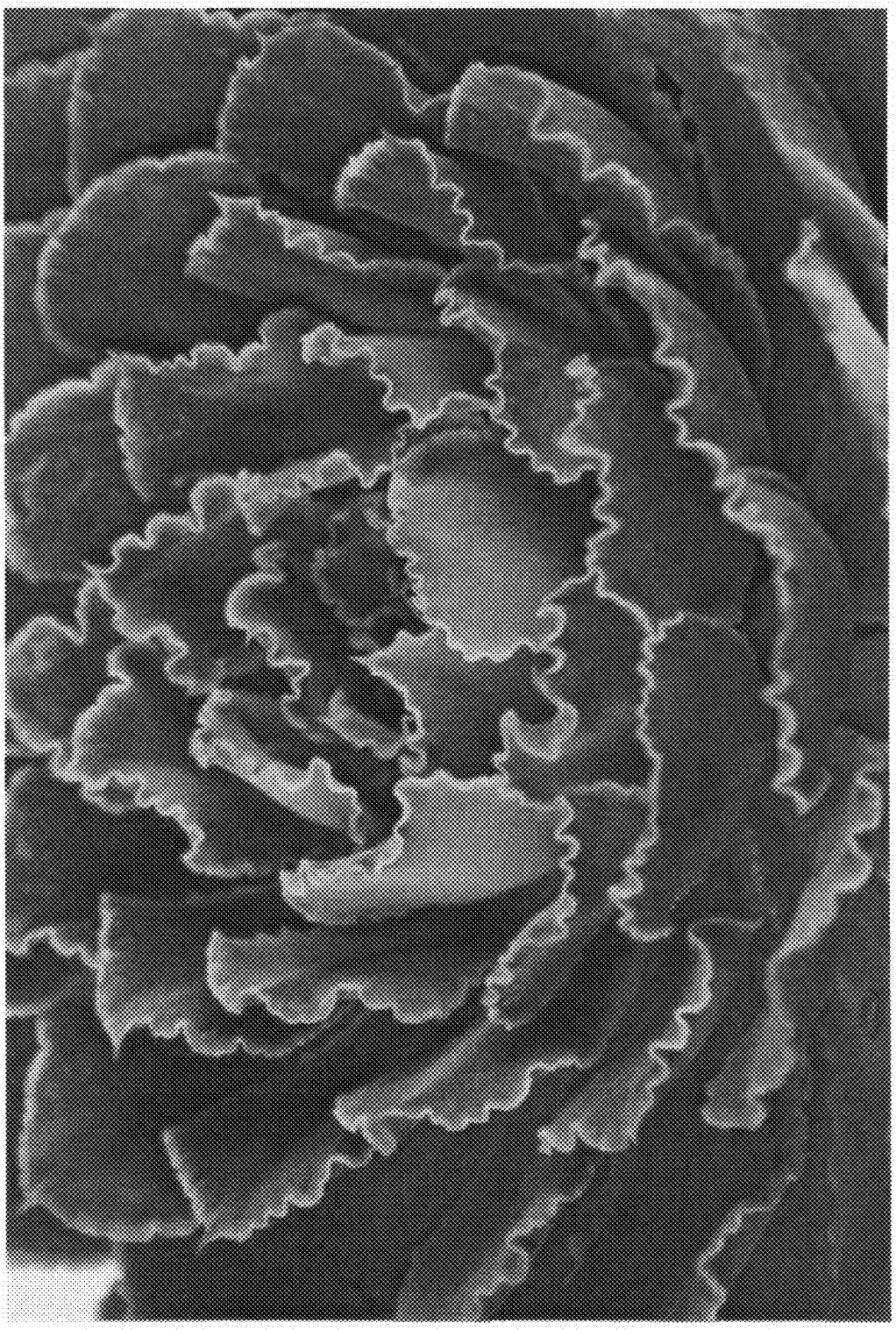

Latin name of the genus and species: *Echeveria* hybrid.
Variety denomination: 'Neon Breakers'.

BACKGROUND OF THE INVENTION

The new cultivar is a product of a planned breeding program. The new variety originated from a cross pollination of the unpatented, species seed parent, *Echeveria shaviana* with the pollen parent an unpatented, proprietary variety of *Echeveria cantexshaviana* referred to as '#00.' The crossing was made during September 2004 in Vista, Calif., at a commercial greenhouse. 'Neon Breakers' was discovered by the inventor, Renee O'Connell, in February 2005, in Vista, Calif. at a commercial greenhouse.

Asexual reproduction of the new cultivar 'Neon Breakers' was first performed in Vista, Calif., at a commercial greenhouse, by vegetative leaf cuttings in February 2005. 'Neon Breakers' has since produced several generations and has shown that the unique features of this cultivar are stable and reproduced true to type.

SUMMARY OF THE INVENTION

The cultivar 'Neon Breakers' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Neon Breakers.' These characteristics in combination distinguish 'Neon Breakers' as a new and distinct *Echeveria* cultivar:

1. Intensely colorful leaf margins.
2. Increased resistance to normal disease and pests encountered in *Echeveria.*
3. Robust growth.
4. Unique continuous growth, not shutting down seasonally, as is typical of *Echveria.*

PARENTAL COMPARISON

Plants of the new cultivar 'Neon Breakers' are similar to the seed parent *Echeveria shaviana* in most horticultural characteristics. However, 'Neon Breakers' exhibits intensely colorful leaf margins not seen on the seed parent. Additionally, plants of 'Neon Breakers' are more robust, growing faster than the seed parent, showing more resistance to diseases and pests than the seed parent, and not discontinuing growth during seasonal shutdown, as seen in *Echeveria shaviana.*

Plants of the new cultivar 'Neon Breakers' are similar to the pollen parent *Echeveria cantexshaviana* '00' in most horticultural characteristics. However, 'Neon Breakers' exhibits intensely colorful leaf margins, that are more crenulate, that are not seen on the pollen parent. Additionally, plants of 'Neon Breakers' grow more rapidly than '00', however, the final plant size of 'Neon Breakers' is smaller than plants of '00' and, 'Neon Breakers' shows more resistance to diseases and pests than the pollen parent.

COMMERCIAL COMPARISON

'Neon Breakers' can be compared to the unpatented commercial variety *Echeveria shaviana* 'Pink Frills.' Plants of *Echeveria shaviana* 'Pink Frills' are similar to plants of 'Neon Breakers' in most horticultural characteristics, however, 'Neon Breakers' exhibits more intensely colorful leaf margins. Additionally, plants of 'Neon Breakers' are more robust, growing faster than 'Pink Frills', and showing more resistance to diseases and pests. 'Neon Breakers' does not discontinue growth during seasonal shutdown, as seen in *Echeveria shaviana* 'Pink Frills'.

'Neon Breakers' can also be compared to the unpatented commercial variety *Echeveria* 'Blue Giant.' Plants of *Echeveria* 'Blue Giant' are similar to plants of 'Neon Breakers' in most horticultural characteristics, however, 'Neon Breakers' exhibits more intensely colorful leaf margins. Additionally, plants of 'Neon Breakers' are more robust, growing faster than 'Blue Giant', and show more resistance to diseases and pests. 'Neon Breakers' does not discontinue growth during seasonal shutdown, as seen in *Echeveria* 'Blue Giant.'

BRIEF DESCRIPTION OF THE PHOTOGRAPH

The accompanying photograph in FIG. 1 illustrates in full color a typical plant of 'Neon Breakers' grown outdoors in Vista, Calif. This plant is approximately 7 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, except where general terms of ordinary dictionary significance are used. The following observations and measurements describe 'Neon Breakers' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.
Botanical classification: *Echeveria* hybrid 'Neon Breakers'.
Age of the plant described: Approximately 6 months.

PROPAGATION

Time to initiate roots: About 20 days at approximately 21° C.
Root description: Fibrous.
Propagation method: Terminal vegetative divisions and leaf cuttings

PLANT

Growth habit: Densely rosulate, sessile succulent.
Container size: 6 inch.
Height: Approximately 6 cm to top of highest leaf.
Plant spread: Approximately 13.5 cm.
Growth rate: Moderately fast.
Branching characteristics: Rarely.

FOLIAGE

Leaf:
- *Arrangement.*—Rosulate.
- *Average length.*—Approximately 6.5 cm.
- *Widest width.*—Approximately 3 cm.
- *Width at base.*—1 cm.
- *Shape of blade.*—Spatulate.
- *Apex.*—Mucronate.
- *Base.*—Rounded.
- *Margin.*—Finely crenulate, undulate crispate.
- *Texture of top surface.*—Glabrous, pruinose.
- *Texture of bottom surface.*—Glabrous, pruinose.
- *Quantity of leaves per plant.*—Approximately 66.
- *Color.*—Young foliage upper side: Middle of leaf, near S 257-6 Pantone. Young foliage upper side: Tip, near S 202-2 Pantone. Young foliage, under side: Near S 257-7 Pantone. Young foliage, margin: Between 128.5 and 128.4 Pantone. Mature foliage upper side: Near S 202-7 Pantone. Mature foliage upper side, near stem: Near S 311-7 Pantone. Mature foliage under side: Near S 202-7 Pantone. Mature foliage under side, near stem: Near S 311-7. Mature foliage, margin: Near S 128-3 Pantone. Mature foliage, margin, near stem: Near S 128-9 Pantone.

Venation:
- *Type.*—Parallel.
- *Venation color upper side.*—Indistinguishable from overall foliage color.
- *Venation color under side.*—Indistinguishable from overall foliage color.

FLOWER

Flowering: Flowering has not been observed to date in the new variety.

OTHER CHARACTERISTICS

Fruits and seeds: Not observed to date.
Temperature tolerance: Tolerates temperatures from approximately −2 C to 32 C.
Disease/pest resistance: Increased resistance to normal diseases and pests of *Echeveria* has been observed.
Drought tolerance: Tolerates at least 2 weeks of high temperatures without supplemental water, showing no serious damage to plant.

What is claimed is:

1. A new and distinct cultivar of *Echeveria* plant named 'Neon Breakers' as herein illustrated and described.

* * * * *